United States Patent [19]

Saihara et al.

[11] Patent Number: 5,380,521
[45] Date of Patent: Jan. 10, 1995

[54] METHOD FOR OBTAINING DEODORANT EXTRACT FROM TISSUE CULTURE OF PLANTS IN FAMILY OLEACEAE

[75] Inventors: Yasuhiro Saihara; Haruyuki Date; Toshiyuki Yamauchi; Manabu Mizobuchi, all of Kadoma, Japan

[73] Assignee: Matsushita Electric Works, Ltd., Osaka, Japan

[21] Appl. No.: 863,359

[22] Filed: Mar. 31, 1992

Related U.S. Application Data

[62] Division of Ser. No. 457,586, Dec. 27, 1989, abandoned.

[51] Int. Cl.⁶ .............. A61K 35/78; A61K 7/32; A01H 4/00
[52] U.S. Cl. .............. 424/76.1; 424/76.3; 424/DIG. 5; 424/195.1; 424/65; 514/783; 435/240.48
[58] Field of Search .............. 424/76.1–76.4, 424/DIG. 5, 195.1; 435/240.48; 514/783

[56] References Cited

U.S. PATENT DOCUMENTS

| | | | |
|---|---|---|---|
| 4,154,817 | 5/1979 | Tsuchiya et al. | 424/76.2 |
| 4,167,559 | 9/1979 | Michel. | |
| 4,170,638 | 10/1979 | Owades. | |
| 4,251,508 | 2/1981 | Monsod, Jr. | |
| 4,617,185 | 10/1986 | Di Pietro | 424/DIG. 5 |
| 4,681,757 | 7/1987 | Mimasu et al. | |
| 4,717,664 | 1/1988 | Hara et al. | 435/133 |
| 4,898,727 | 2/1990 | Osada et al. | 424/76.1 |
| 4,923,809 | 5/1990 | Otsuji et al. | 536/1.1 |

FOREIGN PATENT DOCUMENTS 0066434 of 1978 Japan.
66434 6/1978 Japan.
0264442 of 1985 Japan.
62-219 3/1987 Japan.

OTHER PUBLICATIONS

Kawachi et al., Japan Laid–Open 53–66434.
Yamauchi et al., Application 60-2644442, Laid Open 62-122666, PTO Translation.

Primary Examiner—Edward J. Webman
Attorney, Agent, or Firm—Burns, Doane, Swecker & Mathis

[57] ABSTRACT

A deodorant containing deodorizing ingredients extracted from Oleaceae family plants obtained through a tissue culture by means of a medium with plant growth regulators as cytokinins and/or copper ions added for a highly efficient promotion of production of the deodorizing ingredients within cells of the Oleaceae family plants.

25 Claims, No Drawings

METHOD FOR OBTAINING DEODORANT EXTRACT FROM TISSUE CULTURE OF PLANTS IN FAMILY OLEACEAE

This application is a divisional of application Ser. No. 07/457,586, filed Dec. 27, 1989, now abandoned.

TECHNICAL BACKGROUND OF THE INVENTION

This invention relates to a deodorant which can be mass-produced by means of a tissue culture.

The deodorant of the kind referred to is effective for reducing bad or offensive odors from cigarette smoke, kitchen garbage, excretion and the like, or caused by various types of waste liquid, exhaust gas and discharged smoke of factories, vehicles and so on.

DESCRIPTION OF THE RELATED ART

In recent years, the offensive odors have been taken up as an important issue of life environment contamination and the deodorization is a great social concern, and there have been suggested various methods for reducing the offensive odors. One of these methods is use of fragrant substance as the deodorant for the purpose of masking human sense of smell by means of the fragrance. However, this method is defective in that the fragrant substance is limited in such masking ability and, in particular, in the ability of coping with any strong odor. Further, it is rather difficult to balance the fragrance with the offensive odors, and to achieve a general-purpose deodorizing action since like and dislike vary from person to person. There has been suggested another method, in which air in a limited space of house room or the like is ventilated or diffused, but this method has been still defective in its necessity of resorting to an expensive ventilating or the like device, and in inherent change in the room temperature.

Another method is deodorization by chemical reaction of the offensive odors, but this method requires selection of different chemical substances with respect to different odors in order to cause the effective chemical reaction thereto, which results undesirably in that the selection becomes complicated while various sorts of deodorants must be prepared, lowering application flexibility of the method. With respect to the offensive odor resulting from decomposition and the like, further methods have been suggested for killing bacteria to cause the decomposition to stop and to prevent the offensive odor, but they still involve problems that expensive bactericidal apparatus is required and it takes time until its effect appears.

Meanwhile, there has been proposed in Japanese Patent Appln. Laid-Open Publication No. 53-66434 by J. Kawachi et al a deodorant which requires no expensive installation nor apparatus, and this deodorant uses active deodorization ingredients obtained from plants and, more specifically, contains extracts thermally extracted from raw or dried leaves of Camellia or Cinnamomum Camphor plant with use of organic solvent and/or water. This deodorant is advantageous in that the use of the active deodorization ingredients in plants results in simple and low cost production of the deodorant because of easy availability of the plant, but is disadvantageous in that the deodorizing action on the nitrogen or sulfur compound odor is insufficient. Various prior art using the active deodorization ingredients in plants can be seen in U.S. Pat. Nos. 4,167,559 of G. M. Michel, 4,170,638 of J. L. Owades, 4,251,508 of G. G. Monsod, Jr., and 4,681,757 of T. Mimasu et al, but their deodorants have all a relatively narrow range of odor to deal with and are poor in the application flexibility. On the other hand, K. Osada et al have suggested in U.S. patent application Ser. No. 878,324 a deodorant which realizes the deodorization with ingredients extracted from a species of plants effective with respect to the nitrogen or sulfur compound odor, which shows a remarkable reduction of the offensive odor in particular of the sulfur compound.

While the plants of such species are easily available, they are natural plants and are limited in the growing rate and eventually in the supply amount, so as to be defective in that their constant supply can easily be affected by any change in such natural environmental conditions as wind, rain, temperature and so on. Accordingly, the present inventors have suggested in an earlier Japanese Patent Application No. 60-138377 (Laid-Open Patent Publication No. 62-219) a tissue culture of plants in a genus of Forsythia showing excellent deodorizing effect with respect to the sulfuric compound odor as well as a deodorant employing deodorizing ingredients extracted from the plants thus cultured. The suggested tissue culture is effective to a certain extent to overcome the problems in the limited and unstable supply, but it has been demanded to further improve the efficiency in the culture and the plant supply, so as to sufficiently maintain the supply rate of the deodorizing ingredients.

SUMMARY FIELD OF THE INVENTION

A primary object of the present invention is, therefore, to provide a deodorant containing deodorizing ingredients obtained by improving the efficiency of tissue culture of such plants in the family of Oleaceae as *Forsythia suspensa*.

Another object of the present invention is to provide a deodorant containing deodorizing ingredients obtained at a stable quality from the Oleaceae family plants mass-produced.

Still another object of the present invention is to provide a deodorant consisting of deodorizing ingredients produced by means of a tissue culture and still substantially of equal quality to that of extract from natural plants.

A further object of the present invention is to provide a deodorant capable of being used in any style of spraying liquid, filter impregnation and solid stick.

According to the present invention, the above objects can be realized by a deodorant containing deodorizing ingredients extracted from plants in the family of Oleaceae obtained through a tissue culture with a culture medium containing cytokinins as plant growth regulators and copper ions.

Other objects and advantages of the present invention shall be made clear in following explanation of the invention detailed with reference to preferred examples. It should be appreciated, however, that the present invention is not to be limited only to the examples described but is to include all modifications, alterations and equivalent arrangements possible within the scope of appended claims.

DETAILED DESCRIPTION OF PREFERRED EMBODIMENTS

In the deodorant according to the present invention, deodorizing ingredients extracted from the plants in the family of Oleaceae which are obtained through a tissue culture. For the Oleaceae family plants, there can be employed various plants classified in such genera of the Oleaceae family as Osmanthus, Forsythia, Olea, Syringa, and Fraxinus. While not necessary to limit, the plants in the genera of Osmanthus and Forsythia exhibit excellent deodorizing effect and are preferable. In these plants of Forsythia, further, desirable plants are *Forsythia suspensa*, *Forsythia japonica* Makino, Forsythia Viridissima Lindl and *Forsythia koreana* Nakai. There can be also listed here as optimum plants in Osamanthus such as *Osmanthus fragrans* Lour. Var. Auranlacus Makino, *Osamanthus fragrans* Lout. O. Asiaticus Nakai, *Osmanthus heterophyllus*, Osmanthus X. Fortuneiu Carr and *Osmanthus insulario koidz*.

The culture is to be carried out initially by subjecting to bactericidal treatment such organs as leaves, leafstalks, stalks, roots and so on of the foregoing subject plants in a manner well known. That is, these organs are cut into pieces of about 2 to 3 cm or to be about 2 to 3 cm square, and are then sterilized by an aqueous solution of sodium hypochlorite and ethanol. Thereafter, they are further cut into pieces of about 1 to 2 cm under sterilized condition, and are bedded on a solid medium. Cells for the culture are subjected to an induction of callus on a solid medium (agar), for which medium such generally widely utilized basic medium as Linsmaier & Skoog (LS) or Gomborg B5 or the like is used with agar added. The thus induced callus is transplanted to a liquid medium to carry out the tissue culture. For the liquid medium, while not limited particularly, White's liquid medium should preferably be employed, in view of an excellent effect caused by inorganic components (in particular, N components) contained in the White's medium, due to that secondary metabolism (producing the deodorizing ingredients) is presumably more actively carried out than primary metabolism system of the cells (their multiplication or growth due to production of amino acid and the like) in this medium.

More preferable is that a suspensoid culture with the LS or Gomborg B5 liquid medium is preliminarily carried out prior to the tissue culture by means of the White's medium or the like, and the cells in logarithmic growth phase or in stationary phase of the growth curve are transplanted to the White's medium, for reasons that the transplant of the cells in such phase allows the deodorizing ingredients produced in a shorter period than in a case of transplantation of cells in lag phase, and that, more importantly, a larger amount of cells can be added to the White's medium to render a larger amount of the effective deodorizing ingredients to be eventually obtained. It is proper that the cells thereby obtained are added by 2-20 wt. % to the White's liquid medium.

The amount of the cells contained in the medium as a result of the transplantation is made to be 2 to 20 wt. % in fresh weight of only the cells. While the cells may be transplanted after being separated from the medium by means of a filtration or the like, the cells in the suspensoid culture may be used without being separated from the medium. In that case, the amount of the medium of the suspensoid culture should not exceed the amount of the White's medium of the liquid cultivation. In short, the present invention is to be featured in such two steps as the callus induction with the solid medium and the tissue culture with the liquid medium for the production of the deodorant ingredients or, more preferably, in such three steps as the callus induction with the solid medium, the cell growth with the suspensoid culture, and the tissue culture with the liquid medium for producing the deodorant ingredients.

Procedure of the tissue culture including the induction of callus shall be further explained. While not limited particularly, it is preferable that, to the culture medium, such carbon source or energy source as sugar, glucose or the like, such inorganic salts as calcium chloride or the like, such growth factor as amino acid, vitamins or the like are added. It is also preferable to use in a proper combination such plant growth regulators as auxins and cytokinins. For the auxins, there may be enumerated α-naphthalene-acetic acid, indolylacetic acid, indolebutyric acid, 2,4-dichloro-phenoxyacetic acid and the like and, for the cytokinins, N'-benzoyl adenine, benzyl adenine, kinetin, 2-hydroxypurine, phenyl aminopurine, 6-methylpurine, zeatin and the like may be enumerated.

In using the LS or the like solid medium (with a basic medium of a liquid but made solid with agar added), it is preferable to add thereto $10^{-7}$ to $10^{-5}$M of each of such auxin as α-naphthalene-acetic acid or the like and such cytokinins as kinetin, 0-10 wt. % (with the basic liquid medium made as a reference) of sugar and 0.7-2.0 wt. % (with the basic liquid medium made as a reference) of agar. After inoculation of external plant in the medium with agar added, they are left for the culture for 2 to 3 weeks under a normal temperature, and callus thereby produced is to be employed, In using, on the other hand, the liquid medium for the growth of cells through the culture with the induced callus suspended, it is preferable to add thereto $10^{-7}$ to $10^{-4}$M of auxins, 0 to $10^{-5}$M of cytokinins, and 1-10 wt. % (with the basic liquid medium made as a reference) of sugar. It may be possible to employ only either one of auxins and cytokinins, in which event auxins should preferably be employed. Further, copper ions detailed later may also be added by 0-20 ppm as converted to copper sulfate. By "converted to copper sulfate" is meant the amount in ppm of copper ion in the form of copper sulfate.

At the liquid medium to which callus is transplanted after the foregoing suspension culture, the production of the deodorizing ingredients is mainly carried out the tissue culture is also be carried out, and at least one of cytokinins and copper ions is added here. Because the added amount thereof is determinative to the effective production of the deodorizing ingredients, it is preferable that cytokinins will be about $10^{-7}$ to $10^{-3}$M, and that copper ions will be about 5-100 ppm as converted to copper sulfate, the copper ions being obtainable by an addition of such salt as copper chloride, copper nitrate, copper acetate, copper sulfate and the like. When the added amount of salt is less than 5 ppm, no sufficient effect of providing the copper ions is attainable, while the amount over 100 ppm may cause a risk to arise in hindering the cell from growing.

In extracting the ingredients effective as the deodorant after completion of the culture, it may be sufficient, for example, to filtrate the cells out of the medium and, after a sufficient rinsing, to subject them to an extraction for 0.5 to 5 hours at 20° to 90° C. with water or a mixture solvent of water and alcohol at a ratio of 1:9 to 1:1.

Examples of the present invention shall now be described in the followings, along with comparative example.

EXAMPLES 1-4

Organs of Forsythia koreana Nakai were cut into pieces of 2-3 cm, the cut pieces were sterilized by an aqueous solution of ethanol, external plant sections of 1-2 cm were cut out of the organs under sterilized condition, and they were bedded on the LS solid medium for inducing callus. The LS solid medium used here consisted of $10^{-5}$M of naphthalene-acetic acid, $10^{-7}$M of kinetin, 10 wt. % of sugar and 0.7 wt. % of agar (respectively with the basic liquid medium made as a reference). The plant sections bedded on such solid medium was cultured for 2 weeks at normal temperatures to have callus induced.

Cells in logarithmic growth phase of Forsythia koreana Nakai being cultured in the LS medium (with 3 wt. % sugar and $10^{-6}$M naphthalene-acetic acid added) after the callus induction were transplanted to the White's medium with 3 wt. % sugar added, and pH being 5.6) to which each of such different cytokinins as shown in Table I was added, and the liquid culture was carried out for two weeks. After this culture (cell concentration about 10 wt. %), the cells obtained were subjected to filtration, rinsing and thereafter hot water extraction for 4 hours at 50° C. An extract was diluted to be of 0.1 wt. % concentration with a buffer solution of pH 6.5 (of phosphoric acid), and sample deodorants were obtained.

EXAMPLES 5-7

Except for an addition of copper sulfate instead of cytokinins, further sample deodorants were obtained in the same manner as in the above EXAMPLE 1.

COMPARATIVE EXAMPLE 1

A comparative sample deodorant was obtained from an extract obtained from Forsythia koreana Nakai collected in the month of October. Cell culturing was carried out in the same manner as in the above EXAMPLE 1.

COMPARATIVE EXAMPLE 2

A further comparative deodorant was obtained in the same manner as in the foregoing EXAMPLES 1-7, except for that no such additive as cytokinin and copper sulphate to the liquid medium was used.

A deodorizing test was carried out for the respective deodorants obtained through the EXAMPLES 1-7 and COMPARATIVE EXAMPLES 1 and 2, by means of a gas-chromatograph equipped with a frame photometric detector (FPD-GC). In carrying out the test, 2 ml of the deodorant in liquid phase was sealed within a container of about 10 ml, 1 ml of methyl mercaptan gas dilution-regulated was added by a gas bomb as an odorous gas, they were stirred for 45 minutes, thereafter methyl mercaptan concentration in head space gas was measured, the deodorization rate with respect to water used for a blank test (the deodorization rate with water being 0 wt. %) was calculated, and results were as listed in Table I as follows:

TABLE I

| | Type of Additive | Added Amount | Deodorizing Rate (%) |
|---|---|---|---|
| EX. | | | |
| 1 | N'-benzoyl adenine | $10^{-4}$M | 95 |
| 2 | 2-hydroxypurine | $10^{-3}$M | 94 |
| 3 | Benzyl adenine | $10^{-6}$M | 93 |

TABLE I-continued

| | Type of Additive | Added Amount | Deodorizing Rate (%) |
|---|---|---|---|
| 4 | Zeatin | $10^{-5}$M | 90 |
| 5 | Copper sulfate | 5 ppm | 83 |
| 6 | Copper sulfate | 20 ppm | 91 |
| 7 | Copper sulfate | 100 ppm | 85 |
| COMP. EX. | | | |
| 1 | (natural only) | — | 90 |
| 2 | (no additive) | — | 80 |

It has been thus found that, as will be clear from the above Table I, the deodorants obtained through the respective Examples according to the present invention show a deodorizing effect of the same level as or more than that of the natural one according to COMPARATIVE EXAMPLE 1, and that a remarkably improved deodorizing effect can be attained as compared with COMPARATIVE EXAMPLE 2 employing no such additive as cytokinin or copper sulfate. It has been also found that, with copper sulfate added less than 5 ppm, the deodorant is effective and, even with its addition over 100 ppm, the effect is rather lowered.

EXAMPLES 8-14

Leafstalks of about 1 cm of such various Forsythia genus plants as listed in Table II as follows were subjected to a bactericidal treatment, bedded in an LS solid medium (containing 3 wt. % sugar, $10^{-6}$M naphthalene-acetic acid, $10^{-7}$M kinetin, and 1 wt. % agar), and the callus induction was carried out at 25° C. Callus thus obtained in LS liquid medium with agar in the above composition removed was suspended, 75 ml of such suspension was added in a flask (Meyer) of 300 ml, and the culture and growth were carried out under Meyer's shaking condition of 100 rpm rotation and at 25° C. The cells from latter half of the logarithmic growth phase to the stationary phase in the growth curve were transplanted to the White's medium (containing 3 wt. % sugar) to which a variety of cytokinins such as listed in the following Table II and copper sulfate were added, and further culture was carried out. For the extraction of the deodorizing ingredients from thus cultured cells, these cells were first filtered out of the medium, sufficiently rinsed with water, and thereafter subjected to the hot water extraction for 4 hours at 50° C. and thus obtained extract was concentrated to be solid. The solid extract was prepared into 1 wt. % aqueous solution and made to be a deodorant.

COMPARATIVE EXAMPLES 3-8

As shown in the following Table II, cytokinin and copper sulfate were added as required, and various comparative samples of the deodorants were obtained in the same manner as in the foregoing EXAMPLES 8-14.

In respect of each of the deodorants obtained through the above EXAMPLES 8-14 and COMPARATIVE EXAMPLES 4-8, the deodorizing rate was calculated with water made as the blank, by placing 0.1 ml of the deodorant and 1.9 ml of a buffer solution of phosphoric acid (pH 6.7) in a test tube of 10 ml, adding thereto 1 ml of an odorous gas obtained with methyl mercaptan ($CH_3SH$) and a standard hydrogen sulfide gas ($H_2S$), and measuring residual odorous gas concentration within the test tube after elapsing of 45 minutes by the foregoing FPD-GC, and measured values were as listed in the following Table II:

TABLE II

| | Plant Used | Cytokinin Used | Add. (M) | Copper sulfate (ppm) | Deod. Rate (%) $CH_2SH$ | $H_2S$ |
|---|---|---|---|---|---|---|
| EX. | | | | | | |
| 8 | Forsythia viridissima Lindl | Kinetin | $10^{-3}$ | 5 | 91 | 68 |
| 9 | Forsythia suspensa | Benzyl adenine | $10^{-5}$ | 30 | 90 | 73 |
| 10 | Forsythia koreana Nakai | 2-Hydroxypurine | $10^{-2}$ | 90 | 93 | 72 |
| 11 | Forsythia viridissima Lindl | Phenyl aminopurine | $10^{-7}$ | 20 | 90 | 69 |
| 12 | Forsythia suspensa | 6-Methylpurine | $10^{-4}$ | 100 | 83 | 69 |
| 13 | Forsythia koreana Nakai | N'-Benzoyl adenine | $10^{-5}$ | 10 | 93 | 71 |
| 14 | Forsythia koreana Nakai | Kinetin | $10^{-6}$ | 70 | 92 | 75 |
| COMP. EX. | | | | | | |
| 3 | Forsythia koreana Nakai | N'-Benzoyl adenine | $10^{-6}$ | — | 72 | 53 |
| 4 | Forsythia suspensa | — | — | 30 | 73 | 51 |
| 5 | Forsythia suspensa | Kinetin | $10^{-9}$ | — | 45 | 21 |
| 6 | Forsythia koreana Nakai | N'-Benzoyl adenine | $10^{-4}$ | 150 | (Brown death, of cells) | |
| 7 | Forsythia koreana Nakai | Kinetin | $5 \times 10^{-3}$ | — | 31 | 10 |
| 8 | Forsythia viridissima | — | — | — | 40 | 23 |

It has been found, as will be clear from Table II, that the deodorants obtained through the EXAMPLES 8-14 according to the present invention have been provided with further excellent deodorizing effect by the addition of both of cytokinins and copper sulfate. As will be also clear from the measured values for the deodorants of COMPARATIVE EXAMPLES 3-8 in Table II, the deodorizing effect is rather lowered when these additive members are excessive over a proper range.

According to another feature of the present invention, the deodorizing effect of the deodorant can be further elevated by an addition of glyoxal to the deodorizing ingredients extracted. While the amount by which glyoxal is added is not required to be specifically limited, it is preferable that the adding amount is 0.1–500 parts by weight/1 part by weight with respect to the extract 1. Examples of this feature shall be referred to hereinunder along with Comparative Examples.

EXAMPLES 15 and 16

The deodorizing ingredients were extracted from Osmanthus Lout. Var. Auranlacus Makino and Forsythia suspensa, respectively, in the same manner as in the foregoing EXAMPLE 1, and liquid extracts obtained were concentrated to exsiccation by means of a rotary evaporator. The exsiccated extracts were regulated with a phosphoric acid buffer (0.15M) of pH 4.5 to render the concentration of the deodorizing ingredients to be 0.1 wt. %. To these extracts, 40 wt. % aqueous solution of glyoxal was added, the concentration of this solution was regulated to be of predetermined concentrations of 1 wt. % and 5 wt. %, and two deodorants were obtained.

COMPARATIVE EXAMPLES 9 and 10

The same extracts as in the above EXAMPLES 15 and 16 were prepared to be two deodorants without addition of glyoxal.

The respective deodorants obtained through these EXAMPLES 15 and 16 and COMPARATIVE EXAMPLES 9 and 10 were subjected to an evaluation of the deodorizing effect in such manner that each solution of the respective deodorants was put in a gastight container by a fixed amount, trimethylamine $(CH_3)_3N$ gas and methyl mercaptan $CH_3SH$ gas were led into the container, and then the container was sealed. A mixture gas in head space of this container was thereafter collected, and the concentration of trimethylamine and methyl mercaptan was measured by means of the gas-chromatography. For the detection, FID and FPD were employed, respective odor concentration in the case where water was used instead of the deodorant solutions were measured, and odor removal rate was obtained according to a formula Odor Removal Rate (%) = $\{(A-B)/A\} \times 100$ wherein A was odor concentration in the case where water was used, and B was odor concentration in the case where the deodorant was employed. Thus obtained values were as listed in Table III as follows:

TABLE III

| | Plant | Deod. Ing. Concent. (wt. %) | Glyoxal Concent. (wt. %) | Deodorizing Rate(%) $(CH_3)_3N$ | $CH_3SH$ |
|---|---|---|---|---|---|
| EX. | | | | | |
| 15 | Osmanthus fragrans Lours. Var. Auranlacus Makino | 0.1 | 1.0 | 94 | 89 |
| 16 | Forsythia suspensa | 0.1 | 5.0 | 95 | 93 |
| COMP. EX. | | | | | |
| 9 | Osmanthus fragrans Lours. Var. Auranlacus Makino | 0.1 | — | 67 | 71 |
| 10 | Forsythia suspensa | 0.1 | — | 60 | 77 |

As will be clear from the above Table III, it has been found that the deodorizing effect could have been remarkably increased by the addition of glyoxal to the extracted components from the plants.

EXAMPLES 17 and 18

Deodorizing ingredients were extracted respectively from Osmanthus X. Fortuneiu Carr and Lilac substantially in the same manner as in the foregoing EXAMPLE 1 except that the extraction was carried out at 60° C. for 3 hours, and the extracts were concentrated to exsiccation. Thus extracted ingredients were regulated by phosphoric acid buffer (0.1M) of pH 6.5 so as to be of a concentration of 0.5 wt. %. 40 wt. % aqueous solution of glyoxal was added to the regulated ingredients so that glyoxal concentration would be 0.25 wt. %, and two deodorants were obtained.

COMPARATIVE EXAMPLES 11 and 12

Two deodorants were obtained from the same extracts as in the above EXAMPLES 17 and 18 but without adding thereto any glyoxal.

COMPARATIVE EXAMPLE 13

Phosphoric acid buffer only was employed as a deodorant.

Evaluation of the deodorizing effect was carried out in a following manner with respect to the respective deodorants obtained through the above EXAMPLES 17 and 18 and COMPARATIVE EXAMPLES 11-13. That is, a fixed amount of each solution of the respective deodorants was put in a container, an ammonia solution and hydrogen sulfide solution were added thereto, and the container was sealed. Thus obtained test samples were subjected to human discrimination of odor intensity by five panelists having the same degree of the sense of smell, with six grades of the evaluation giving point "0" to no smell, "1" to very slight smell, "2" to slight smell, "3" to easily sensible, "4" to strong smell, and "5" to very strong smell, results of which evaluation were as shown in a following Table IV in the average value of the five panelists.

TABLE IV

| Average Odor Intensity by 5 Panelists | EXAMPLE | | COMPARATIVE EXAMPLE | | |
|---|---|---|---|---|---|
| | 17 | 18 | 11 | 12 | 13 |
| Ammonia | 0.8 | 1.2 | 1.2 | 1.8 | 4.2 |
| Hydrogen Sulfide | 0.8 | 1.4 | 1.0 | 1.4 | 4.4 |

In view of the above Table IV, it has been found that the deodorizing effect could be improved to a large extent by the addition of glyoxal. As a result of the same test carried out as in the foregoing EXAMPLES 15-18 with respect to other odor elements than the above two, it has been also found that excellent effect could be attained for any one of them. It has been further found that the addition of glyoxal caused no variation in color phase of the deodorant solutions nor any precipitation even after being left for a long time, and a sufficient stability for a time elapsing could be obtained.

According to still another feature of the present invention, there can be provided a deodorant which is improved in the deodorizing effect by an addition to the extracted deodorizing ingredients at least one organic acid selected from a group consisting of L-tartaric acid, maleic acid, succinic acid, malic acid, citric acid and lactic acid or the like, and/or one inorganic acid selected from a group consisting of phosphoric acid, boric acid and carbonic acid or the like, together with glyoxal and a surface active agent. In this case, the addition of the organic acid strengthens the deodorizing power with respect to nitrogenous odors. While not required to be limited specifically, the amount in which the organic acid is to be added should preferably be 0.1 to 250 parts by weight (in total when a plurality of the organic acids are employed) with respect to 1 part by weight of the extracts. Further, the addition of glyoxal allows the foregoing action as has been described with reference to EXAMPLES 8-18 to be attained, and its optimum adding amount should be, when represented in the part by weight, 0.1 to 500 parts by weight with respect to 1 part by weight of the extracts. With the addition of the surface active agent, further, the deodorant can be maintained to be uniform and also can be provided with a preservative effect. For the surface active agent, i.e., surfactant cationic or amphoteric surface active agent, can be used, and its type is not specifically limited. While its amount of addition is also not required to be specifically limited, the amount may be in a range of 0.1-10 parts by weight with respect to 1 part by weight of the extracts, and the agent should preferably be benzalkonium chloride, cetyl pyridinium chloride, benzethonium chloride or the like as the cationic surfactant, or alkyl polyaminoglycine or the like as the amphoteric surfactant.

In order to further elevate the deodorizing effect of the deodorant prepared, further, it is desirable to regulate the deodorant to be of a pH in a range of 3 to 8 by means of, for example, an addition of an alkaline solution such as sodium hydroxide, potassium hydroxide or the like, a solution having a buffer action such as a phosphoric acid buffer or the like.

EXAMPLES 19-26

Deodorizing ingredients were extracted from such plants as listed in Table V as follows in the same manner as in the foregoing EXAMPLE 1, thereby obtained liquid extracts were concentrated for exsiccation by means of a Lawry's evaporator or a freezing dryer, and solid extracts were obtained. With such extracts, water, an organic acid, glyoxal and cetyl pyridinium chloride as a surface active agent were added and mixed, sodium hydroxide was added to thus obtained aqueous solutions, pH of which solutions was regulated to be such predetermined values as shown in a following Table V. Ethanol was added at such various amounts as shown in a following Table V to the respective solutions pH-regulated, and sample deodorants of EXAMPLES 19-26 were obtained.

In the following Table V, the amount of ethanol added is presented in the part by weight with respect to 1 part by weight of liquid state mixture of ethanol with the plant extracts, organic acid, glyoxal and so on, pH of which has been regulated.

COMPARATIVE EXAMPLE 14

A sample deodorant was obtained substantially in the same manner as in EXAMPLE 19 except for that lactic acid was not added.

COMPARATIVE EXAMPLE 15

A sample deodorant was obtained substantially in the same manner as in EXAMPLE 19 except for that glyoxal was not added.

COMPARATIVE EXAMPLE 16

A sample deodorant was obtained substantially in the same manner as in EXAMPLE 19 except for that cetyl pyridinium chloride as the surface active agent was not added.

COMPARATIVE EXAMPLE 17

A sample deodorant was obtained substantially in the same manner as in EXAMPLE 19 except for that lactic acid, glyoxal and cetyl pyridinium were not added at all.

COMPARATIVE EXAMPLE 14 having no organic acid is lower in the power of deodorizing the nitrogen series odor, the one of COMPARATIVE EXAMPLES 15 with no glyoxal added is low in the power of deodorizing the sulfur series odor, the one of COMPARATIVE EXAMPLE 16 with no surface active agent added is low in the deodorizing power for both of the nitrogen and sulfur series odors, and the one of COMPARATIVE EXAMPLE 17 is considerably low in the deodorizing power for both of the nitrogen and sulfur series odors. The same panelists' test as in the above has been also carried out with respect to such other odors

TABLE V

| | Plant Species | Concent. of Extracts (wt. %) | Organic Acid Used | Concent. (wt. %) | Concent. of Glyoxal (wt. %) | Concent. of Sur. Act. Agt. (wt. %) | pH | Amt. of Ethanol Added |
|---|---|---|---|---|---|---|---|---|
| Example | | | | | | | | |
| 19 | *Osmanthus fragrans* Lour. Var. Auranlacus Makino | 0.25 | Lactic Acid | 0.4 | 0.6 | 0.2 | 4 | 24 |
| 20 | *Forsythia suspensa* | 0.002 | Lactic Acid | 0.5 | 0.8 | 0.004 | 4 | 24 |
| 21 | *Osmanthus fragrans* L.V.A. Makino | 5.0 | Lactic Acid & Succinic Acid | 0.5 | 0.5 | 0.05 | 5 | 49 |
| 22 | *Forsythia suspensa* | 0.002 | Lactic Acid | 0.5 | | | | |
| 23 | *Oxalis Corniculata* | 0.1 | Malic Acid | 0.125 | 5.0 | 0.01 | 4 | 9 |
| 24 | *Gynko biloba* | 0.01 | L-tartaric Acid | 0.1 | 2.5 | 0.05 | 3 | 1 |
| 25 | *Syringa Vulgaris* | 1.0 | Citric Acid | 0.5 | 5.0 | 0.05 | 3 | 0.5 |
| 26 | *Osmanthus fragrans* L.V.A. Makino | 0.05 | Maleic Acid | 0.25 | 1.0 | 0.005 | 4 | 99 |
| COMP. Ex. | | | | | | | | |
| 14 | *Osmanthus fragrans* L.V.A. Makino | 0.25 | — | — | 0.6 | 0.2 | 4 | 24 |
| 15 | *Osmanthus fragrans* L.V.A. Makino | 0.25 | Lactic Acid | 0.4 | — | 0.2 | 4 | 24 |
| 16 | *Osmanthus fragrans* L.V.A. Makino | 0.25 | Lactic Acid | 0.4 | 0.6 | — | 4 | 24 |
| 17 | *Osmanthus fragrans* L.V.A. Makino | 0.25 | — | — | — | — | — | — |

The respective sample deodorants obtained through the above EXAMPLES 19–26 and COMPARATIVE EXAMPLES 14–17 were subjected to the deodorizing test after leaving them as they stood for 24 hours. That is, a fixed amount of each of the sample deodorants was put in a container as atomized, ammonia gas, hydrogen sulfide gas or methyl mercaptan gas was added thereto to a level providing a very strong odor, and the container was sealed. The same human discrimination of the intensity of odor with the six grade evaluation of "0" to "5" as in the foregoing EXAMPLES 17 and 18 and COMPARATIVE EXAMPLES 11–13 was carried out by five panelists having the same level of the sense of smell, results of which were as shown in Table VI in the following, in average value:

TABLE VI

| Average Odor Intensity by 5 Panelists | Example | | | | | | | | Comp. Example | | | |
|---|---|---|---|---|---|---|---|---|---|---|---|---|
| | 19 | 20 | 21 | 22 | 23 | 24 | 25 | 26 | 14 | 15 | 16 | 17 |
| NH$_3$ | 0.8 | 0.4 | 1.2 | 0.8 | 1.0 | 0.4 | 0.2 | 0.8 | 1.8 | 0.8 | 1.0 | 2.0 |
| H$_2$S | 0.8 | 1.2 | — | — | — | — | — | — | — | — | — | — |
| CH$_3$SH | 0.8 | — | 0.4 | 0.0 | 0.4 | 1.2 | 1.0 | 0.8 | 0.8 | 1.6 | 1.0 | 1.8 |

It has been found as would be clear from the above Table VI that, according to the present feature, the offensive odor of nitrogen series and sulfur series could be deodorized to the level of no smell or at least very slight smell, whereas the deodorants of the Comparative Examples were much deteriorated in the deodorizing power as compared with those of the present feature. That is, it will be appreciated that the deodorant of than the above as trimethyl amine, nicotine and lactic acid, excellent results could be attained with the deodorants of the present feature. In addition, a state observation of the deodorants according to the present feature has shown results excellent in the stability for the time elapsing, without involving any variation in color phase or precipitation.

Aspects in which the deodorants according to the present invention as has been described are utilizable can be selected over such a wide range as a liquid agent, spraying agent, impregnation in a proper carrier, powdery agent, tablets, granular agent and so on, depending on the use and environment in use. When the deodorant is used as the spraying liquid sealed in cans (with any known canning method employed), and as the impregnation in a filtering member or stick, its possibility of general use is more improved.

In using the deodorant according to the present invention in the aspect of the spraying agent, the deodorant obtained through the process as has been described can be utilized as it is, while any proper additive or additives may be added for the purpose of improving deodorizing effect or preservability in the canned state of the agent. In this case, a preferable composition will be of the deodorant, organic and/or inorganic acid, glyoxal and the surface active agent, pH of which should desirably be adjusted to be in a range of pH 3–8 with any agent admixed as has been described. In preparing the spraying agent, further, it is preferable to add ethanol to the deodorant composition at 0.1 to 99 times by weight of total weight of the composition of other components than ethanol.

What is claimed is:

1. A method for obtaining a deodorant extract from a plant material in the family Oleaceae, which method comprises the steps of:
   (a) taking a portion of a plant of the family Oleaceae and culturing said plant portion on a solid medium to induce the formation of callus;
   (b) transferring the resulting plant cells with induced callus to a liquid medium which contains a cytokinin and copper ions in an amount sufficient to increase the amount of deodorant materials contained in the plant cells, and culturing said plant cells in said liquid medium in a single liquid medium stage for a time period sufficient to increase the amount of deodorant materials contained in the plant cells, the amount of cells transferred comprising from 2-20 wt. % of the liquid medium,
   said cytokinin being selected from the group consisting of N'-benzoyl adenine, 6-benzyl adenine, kinetin, 2-hydroxypurine, zeatin and mixtures thereof and being present in the range of from $10^{-7}$ to $10^{-3}$M, and
   said copper ions being provided by the addition of a compound selected from the group consisting of copper sulfate, copper nitrate, copper chloride, copper acetate and mixtures thereof, in an amount of from 5 to 100 ppm on a copper sulfate basis; and
   (c) removing the plant cells from the liquid medium and extracting the deodorant materials from the plant cells.

2. The method of claim 1 wherein the solid medium includes agar and either an LS or Gomborg B5 medium.

3. The method of claim 1, wherein an organic and/or inorganic acid is added to the extract obtained from step(c).

4. The method of claim 3, wherein the organic acid is selected from the group consisting of lactic acid, succinic acid, malic acid, tartaric acid, citric acid and mixtures thereof, and the inorganic acid is selected from the group consisting of phosphoric acid, boric acid, carbonic acid and mixtures thereof.

5. The method of claim 3 wherein a pH regulator is added to the extract obtained from step (c).

6. The method of claim 5, wherein the pH regulator is selected from the group consisting of sodium hydroxide, potassium hydroxide, a phosphoric acid buffer, and mixtures thereof.

7. The method of claim 1 wherein glyoxal is added to the extract obtained from step (c).

8. The method of claim 1 wherein a surfactant is added to the extract obtained from step (c).

9. The method of claim 1 wherein an organic acid and/or inorganic acid, glyoxal, a surfactant, and a pH regulator which regulates pH within the range of 3-8 is added to the extract obtained from step(c).

10. The method of claim 9 wherein the surfactant is selected from the group consisting of cationic and amphoteric surfactants.

11. The method of claim 9 wherein the surfactant is selected from the group consisting of benzalkonium chloride, cetyl pyridinium chloride, benzetonium chloride and alkyl polyaminoglycine.

12. The method of claim 1 wherein the Oleaceae plant is from a genera selected from the group consisting of Osmanthus, Forsythia, Olea, Syringa, and Fraxinus.

13. The method of claim 1 wherein the solid medium in step (a) further includes a material selected from the group consisting of auxins, cytokinins, and sugar.

14. The method of claim 13 wherein the amount of auxins and cytokinins is $10^{-7}$ to $10^{-5}$M, the sugar is 0 to 10 wt. %, and the agar is 0.7 to 20 wt % of the solid medium.

15. The method of claim 13, wherein the auxin is selected from the group consisting of α-naphthaleneacetic acid, indolebutyric acid, 2,4-dichloro-phenoxyacetic acid and mixtures thereof.

16. The method of claim 13 wherein the cytokinin is at least one selected from the group consisting of N'-benzoyl adenine, benzyl adenine, kinetin, 2-hydroxypurine and zeatin and which is added to a concentration of $10^{-7}$ to $10^{-3}$M.

17. The method of claim 1, wherein the liquid medium in step (b) is White's liquid medium.

18. The method of claim 1, wherein the liquid medium of step (b) includes the step of adding auxin at a concentration lower than that of said cytokinins.

19. The method of claim 18 wherein the amount of auxin is $10^{-7}$ to $10^{-3}$M.

20. The method of claim 19 wherein the medium further includes 1 to 10 wt. % of sugar.

21. The method of claim 19, wherein the auxin is selected from the group consisting of α-naphthaleneacetic acid, indolebutyric acid, 2,4-dichloro-phenoxyacetic acid, and mixtures thereof.

22. A method for obtaining a deodorant extract from a plant material in the family of Oleaceae, which method comprises the steps of:
   (a) taking a portion of a plant of the family of Oleaceae and culturing said plant portion on a solid medium culture bed to induce the formation of a callus in plant cells on a mass-production scale;
   (b) transferring the resulting plant cells with said induced callus to a liquid medium culture bed which contains a cytokinin and copper ions in amounts effective to propagate deodorant materials contained in the plant cells, for culturing said plant cells in said liquid medium in a single liquid medium stage for a time period effective to propagate said deodorant materials contained in the plant cells, the amount of cells transferred comprising from 2-20 wt. % of the liquid medium,
   said cytokinin being selected from the group consisting of N'-benzoyl adenine, 6-benzyl adenine, kinetin, 2-hydroxypurine, zeatin and mixtures thereof and being in the range of $10^{-7}$ to $10^{-3}$M, and
   said copper ion being provided by the addition of a compound selected from the group consisting of copper sulfate, copper nitrate, copper chloride, copper acetate and mixtures thereof in an amount of 5 to 100 ppm on a copper sulfate; and
   (c) removing the plant cells from the liquid medium culture bed, extracting the deodorant materials from the plant cells, and adding to said deodorant material extracted an organic acid and/or inorganic acid, glyoxal, a surfactant, and a pH regulator which regulates pH within the range of 3-8.

23. A method for obtaining a deodorant extract from a plant material in the family Oleaceae, which method comprises the steps of:

(a) taking a portion of a plant of the family of Oleaceae and culturing said plant portion on a solid medium to induce the formation of callus;

(b) transferring the resultant plant cells with induced callus to a first liquid medium selected from the group consisting of LS medium and Gomborg B5 medium;

(c) further transferring the plant cells and callus cultured at step (b) to a second liquid medium containing a cytokinin and copper ions in an amount sufficient to increase the amount of deodorant materials contained in the plant cells, for culturing said plant cells for a time period sufficient to increase the amount of deodorant materials contained in the plant cells, the amount of cells transferred comprising from 2–20 wt. % of the second liquid medium, said cytokinin being selected from the group consisting of N'-benzoyl adenine, 6-benzyl adenine, kinetin, 2-hydroxypurine, zeatin and mixtures thereof and being present in the range of from $10^{-7}$ to $10^{-3}$M, and said copper ions being provided by the addition of a compound selected from the group consisting of copper sulfate, copper nitrate, copper chloride, copper acetate and mixtures thereof, in an amount of from 5 to 100 ppm on a copper sulfate basis; and (d) removing the plant cells from the second liquid medium and extracting the deodorant materials from the plant cells.

24. The method of claim 23, wherein said second liquid medium comprises an additive selected from the group consisting of auxins, sugar, and mixtures thereof, said auxins being added to a concentration of $10^{-7}$ to $10^{-4}$M and said sugar being added in a range from 1 to 10 wt. %.

25. The method of claim 24, wherein the auxin is selected from the group consisting of α-naphthaleneacetic acid, indolebutyric acid, 2,4-dichloro-phenoxyacetic acid and mixtures thereof.

* * * * *